(12) United States Patent
Talman et al.

(10) Patent No.: US 7,878,208 B2
(45) Date of Patent: Feb. 1, 2011

(54) METHOD AND APPARATUS FOR DETERMINING A CHARACTERISTIC OF AN IN VIVO SENSOR

(75) Inventors: James R. Talman, Crofton, MD (US); Shuvo Roy, Shaker Heights, OH (US); Brian L. Sauer, Parma, OH (US); Aaron J. Fleischman, University Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1245 days.

(21) Appl. No.: 11/441,854

(22) Filed: May 26, 2006

(65) Prior Publication Data

US 2007/0038051 A1 Feb. 15, 2007

Related U.S. Application Data

(60) Provisional application No. 60/685,294, filed on May 27, 2005.

(51) Int. Cl.
*A61B 19/00* (2006.01)
(52) U.S. Cl. ...................... 128/899; 600/302
(58) Field of Classification Search .............. 128/899; 600/302, 561
See application file for complete search history.

(56) References Cited

U.S. PATENT DOCUMENTS

| 2,681,434 | A | | 6/1954 | Wheeler | |
|---|---|---|---|---|---|
| 5,196,796 | A | * | 3/1993 | Misic et al. ............. | 324/322 |
| 5,942,991 | A | * | 8/1999 | Gaudreau et al. ......... | 340/870.16 |
| 5,967,986 | A | | 10/1999 | Cimochowski et al. | |
| 6,194,900 | B1 | | 2/2001 | Freeman et al. | |
| 6,579,235 | B1 | | 6/2003 | Abita et al. | |
| 6,682,480 | B1 | | 1/2004 | Habib et al. | |
| 2002/0024450 | A1 | * | 2/2002 | Townsend et al. ......... | 340/870.16 |
| 2002/0143268 | A1 | * | 10/2002 | Meredith et al. ............. | 600/552 |
| 2002/0147416 | A1 | | 10/2002 | Zogbi et al. | |
| 2005/0165317 | A1 | | 7/2005 | Turner et al. | |

FOREIGN PATENT DOCUMENTS

WO WO 93/03391 2/1993

OTHER PUBLICATIONS

Baldi et al., "A Self-Resonant Frequency-Modulated Micromachined Passive Pressure Transensor", *IEEE Sensors Journal*, vol. 3, No. 6, Dec. 2003, pp. 728-733, XP001047496.
Talman et al., "Orthogonal-Coil RF Probe for Implantable Passive Sensors", *IEEE Transactions on Bio-Medical Engineering*, vol. 53, No. 3, Mar. 2006, pp. 538-546, XP002407799.

* cited by examiner

*Primary Examiner*—Charles A Marmor, II
*Assistant Examiner*—Carrie Dorna
(74) *Attorney, Agent, or Firm*—Tarolli, Sundheim, Covell & Tummino LLP

(57) ABSTRACT

Methods and systems are provided for determining a characteristic of an in vivo sensor. A transmit field, operative to induce a response signal in an associated in vivo sensor, is generated at a transmitting component having an associated orientation. The response signal is received at a receiving component, having an associated orientation. The coupling between the transmitting component and the receiving component is measured. The associated orientation of at least one of the transmitting component and the receiving component is rotated as to reduce the measured coupling.

9 Claims, 5 Drawing Sheets

METHOD AND APPARATUS FOR DETERMINING A CHARACTERISTIC OF AN IN VIVO SENSOR

RELATED APPLICATION

This application claims priority from U.S. provisional patent application Ser. No. 60/685,294, filed May 27, 2005, the subject matter of which is incorporated herein by reference.

FIELD OF THE INVENTION

The present invention relates to an apparatus and method for in vivo sensing and, in particular, is directed to a method and apparatus for determining a characteristic of an in vivo sensor.

BACKGROUND OF THE INVENTION

Information regarding the conditions inside a body cavity in a patient, such as a human, can be very helpful to a physician treating the patient. For example, it is desirable to monitor intracranial pressure to look for problems such as hemorrhaging and tumors. As another example, it is also desirable to monitor the pressure inside various blood vessels in the human body to help determine if a problem, such as stenosis or an aneurysm, exists. Due to the difficulties of providing power to a device within the body, passive sensors are often used for in vivo sensing. Passive sensors can be fabricated to detect pressure, temperature, pH, etc, by causing one element of the resonant circuit to change in response to the quantity being detected. This changes the resonant frequency of the device, and this change in resonant frequency can be detected externally using a radiofrequency (RF) probe.

Microelectromechanical systems, or MEMS, are a class of miniature electromechanical components and systems that are fabricated using techniques originally developed for fabricating microelectronics. MEMS devices, such as pressure sensors and strain gauges, manufactured using microfabrication and micromachining techniques can exhibit superior performance compared to their conventionally built counterparts, and are resistant to failure due to fatigue, corrosion, etc. Further, due to their extremely small size, MEMS devices can be utilized to perform functions in unique applications, such as the human body, that were not previously feasible using conventional devices Recently there has been considerable interest in exploiting microelectromechanical system (MEMS) technology to simplify the fabrication and reduce the cost of in vivo sensors. In many implementations, the RF probe used to detect the resonant frequency of a passive sensor uses a "grid-dip oscillator" approach. An oscillating RF current flows through an RF coil, inducing currents in the inductance coil of a nearby sensor. The loading effect of the sensor on the RF transmit coil results in a decrease or "dip" in the phase response of the transmitter current and the frequency at which this occurs is used to deduce the value of the quantity being measured. This method benefits from the simplicity of a single RF coil, but frequency measurements are complicated by difficulties associated with separating the small receive signal from the large oscillation signal.

SUMMARY OF THE INVENTION

In accordance with one aspect of the present invention, a method is provided for determining a characteristic of an in vivo sensor. A transmit field, operative to induce a response signal in an associated in vivo sensor, is generated at a transmitting component having an associated orientation. The response signal is received at a receiving component, having an associated orientation. The coupling between the transmitting component and the receiving component is measured. The associated orientation of at least one of the transmitting component and the receiving component is rotated as to reduce the measured coupling.

In accordance with another aspect of the invention, a radio frequency (RF) probe assembly is provided for determining a characteristic of an associated in vivo sensor. A transmit coil produces an excitation signal, having a first orientation, to excite the in vivo sensor to produce a response signal. A receive coil produces a current in response to the response signal. The receive coil is oriented as to interact with signals having a second orientation that is substantially orthogonal to first orientation. A coupling measurement element detects magnetic coupling between the transmit coil and the receive coil. A rotation element rotates at least one of the receive coil and the transmit coil.

In accordance with another aspect of the present invention, a radio frequency (RF) probe assembly for determining a characteristic of an associated in vivo sensor. A transmit coil produces an excitation signal, having a first orientation, to excite the in vivo sensor to produce a response signal. A receive coil produces a current in response to the response signal. The receive coil is oriented to interact with magnetic fields having a second orientation substantially orthogonal to the first orientation. A coupling measurement element detects magnetic coupling between the transmit coil and the receive coil. A rotation element interacts with the excitation signal produced at the transmit coil as to adjust the first orientation.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

The present invention relates to an apparatus and method for in vivo measurement of one or more characteristics of interest and, in particular, is directed to a method and apparatus for interrogating an in vivo sensor to determine a characteristic impedance or resonance quality factor associated with the in vivo sensor. Potential biomedical applications for the present invention include blood flow and pressure sensors in the vicinity of stents, intraocular pressure sensing for detection of glaucoma, pressure or strain sensors for assessing the progress of spinal fusion procedures, and pressure sensors for monitoring a patient during treatment of hydrocephalus and abdominal aortic aneurysms.

Figure 1:
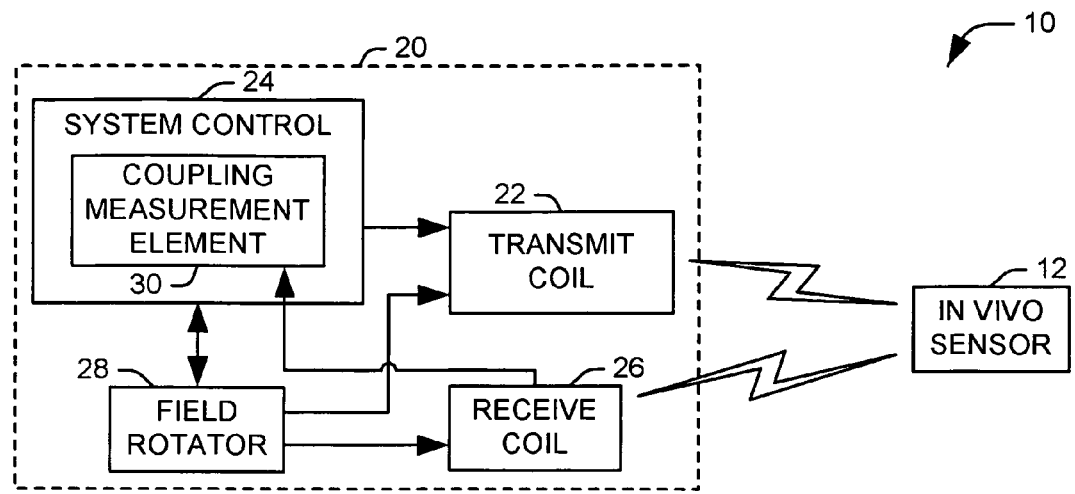
FIG. 1 illustrates a system for determining a characteristic of an in vivo sensor in accordance with an aspect of the present invention.

As representative of the present invention, FIG. 1 illustrates a system 10 for determining a characteristic of an in vivo sensor 12. For example, the in vivo sensor 12 can comprise a tank circuit sensor having an impedance dependent on an internal characteristic of the body in which it is implanted, such as pressure. Alternatively, a quality factor (Q), associated with the resonant circuit within the in vivo sensor 12, can be made dependent on pressure or another internal characteristic of the body. The quality factor is defined as the ratio of the inductive reactance of the inductor to the effective resistance of the inductor or the reactance of the circuit to the effective resistance of the circuit. The system includes an RF probe assembly 20 that excites the in vivo sensor 12 and detects a response signal from the sensor. This response signal is analyzed at the probe to determine the desired characteristic of the sensor 12.

The RF probe 20 includes a transmit coil 22 that provides an excitation signal to the sensor 12 at a frequency determined by a system control 24. For example, the excitation signal can comprise a magnetic field or electromagnetic radiation having a first associated orientation. The excitation signal is received at the in vivo sensor 12, which produces a response signal. For example, the excitation signal can induce the response signal in the in vivo sensor 12. The power of the response signal will reach a maximum when the frequency of the excitation signal equals the resonant frequency of the sensor 12. The resonant frequency of the sensor 12 is, in turn, a function of the characteristic impedance of the sensor 12. The response signal is then received at a receive coil 26, oriented to receive fields or signals having a second orientation, and provided to the system control 24 for analysis. The second orientation is roughly orthogonal to the first orientation associated with the transmit coil.

Accordingly, the system control 24 can sweep the frequency of the excitation signal through a frequency range of interest. As discussed above, the power of the response signal will increase as the frequency of the excitation signal approaches the resonant frequency of the sensor 12. The system control 24 can record the power of the response signal at each excitation frequency across the frequency range of interest. The resulting frequency response will have a peak near the resonant frequency of the sensor 12 and a reasonably flat response elsewhere, forming a reasonably low level noise floor at the remaining frequencies. The width of the peak within the frequency response is a function of a quality factor associated with the in vivo sensor 12. Accordingly, the quality factor can be determined according to an appropriate measure of the peak width (e.g., peak width at half maximum). Among other factors, the noise floor can be a function of coupling between the coils. This coupling is a function of the relative orientation of the fields associated with the coils, with the noise floor being minimized when the associated fields are perfectly orthogonal, thus minimizing the mutual inductance of the transmit and receive coils.

In accordance with an aspect of the present invention, the coupling between the two coils 22 and 26 can be determined at a coupling measurement element 30. In an exemplary embodiment, the coupling measurement element 30 can be located at the system control 24. For example, a range of frequencies that are unlikely to contain the resonant frequency of the sensor 12 can be sampled and provided to the coupling measurement element 30 to determine a noise floor for the probe 20. The relative orientation of the field or signal generated by the transmit coil 22 or received at a receive coil 26 can be changed by a field rotator 28. For example, the field rotator 28 can physically rotate either the transmit coil 22 or the receive coil 26. Alternatively, a magnetic element associated with the probe can be rotated to alter the orientation of one of the fields. The amount of coupling can be sampled at each of a plurality of orientations to determine a field orientation associated with a minimum coupling, representing a position of maximum of orthogonality for the fields.

Figure 2:
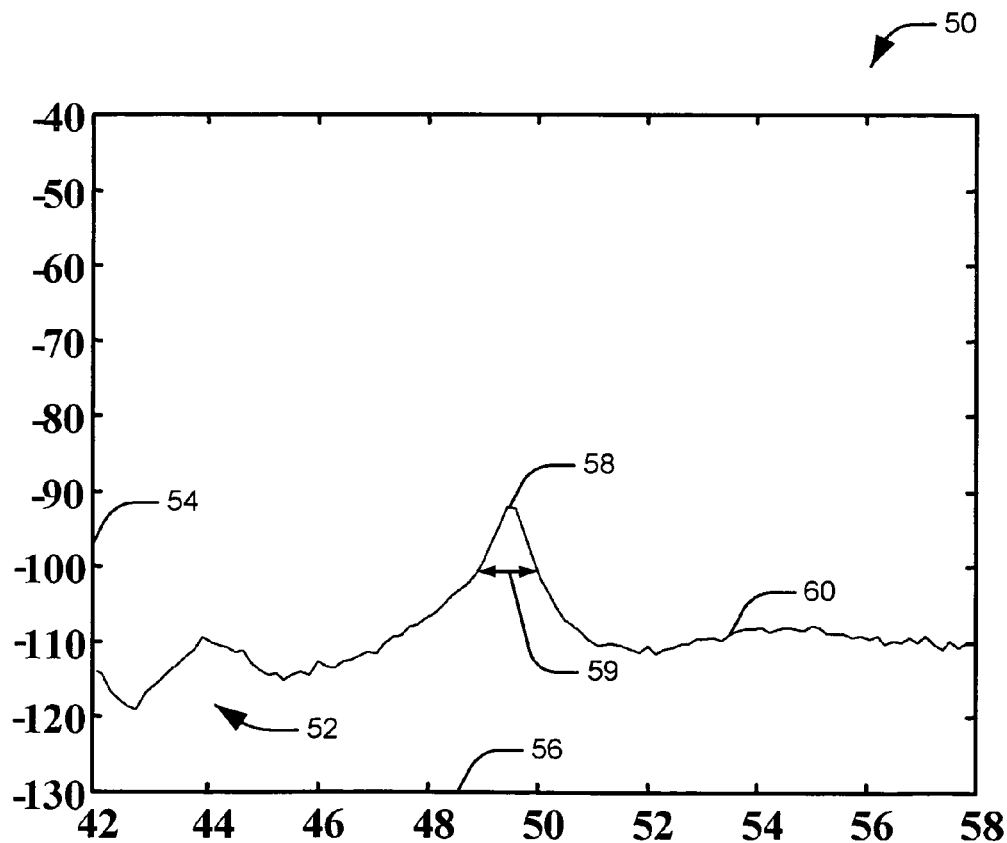
FIG. 2 illustrates a chart of an exemplary frequency response of an in vivo sensor to an excitation signal from an associated probe in accordance with an aspect of the present invention.

FIG. 2 illustrates a chart 50 of an exemplary frequency response 52 of an in vivo sensor to an excitation signal from an associated probe in accordance with an aspect of the present invention. The frequency response 52 is plotted on a vertical axis 54, representing the magnitude, $V_{out}$, of the response in decibels (dB) relative to a reference magnitude, $V_{ref}$, and a horizontal axis 56, representing the frequency of the excitation signal in MHz. The frequency response 52 rises to a peak power 58 at a resonant frequency, $f_r$. The peak associated with the resonant frequency has an associated peak width 59 that is a function of a quality factor associated with the in vivo sensor. At all other points, the frequency response remains at or around a noise floor 60 associated with the probe. Accordingly, an analysis of the frequency response 52 for the probe can provide an indication of a level of noise associated with the probe, the resonant frequency, and an associated quality factor of the in vivo circuit. One or more characteristics of the environment in which the in vivo sensor is implanted can be determined from these qualities according to the design of the in vivo sensor.

Figure 3:
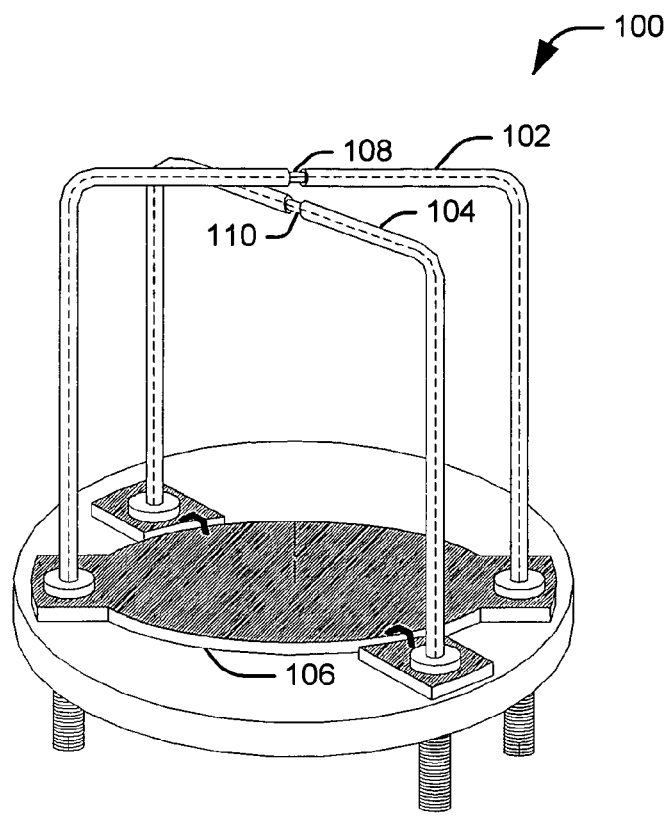
FIG. 3 illustrates an exemplary embodiment of an RF probe in accordance with an aspect of the present invention.

FIG. 3 illustrates an exemplary embodiment of an RF probe 100 in accordance with an aspect of the present invention. The probe 100 consists of two orthogonal shielded loops, a transmit loop 102 and a receive loop 104. The loops can comprise any appropriate implementation of a transmission line, such as a coaxial cable. A swept-frequency transmit signal from a system control is applied to the transmit loop 102, and a response signal received at the receive loop 104 is displayed. In the absence of a nearby resonator, the response signal is a greatly reduced version of the transmit signal due to the inherent spatial isolation between the orthogonal transmit and receive loops 102 and 104. Since it is preferable to minimize the size of sensors used inside of the human body, it is important to maintain the orthogonality of the loops so that the probe 100 can measure the relatively weak response signal that can be expected from smaller sensors.

Due to machining tolerances, it is not possible to fabricate a probe with perfect isolation between transmit and receive loops 102 and 104. For example, existing probes may achieve an interference "floor" that is only 60 dB below the level of the transmitted signal when the signal is transmitted at 50 MHz. This level is insufficient to detect small implanted sensors (e.g., 5-10 mm) because the re-radiated response signal from the sensor is smaller than the interference floor. However, by allowing minor rotation of one of the loops (e.g., 104) with respect to the other, significantly better isolation, on the order of 100 dB, can be obtained.

Each shielded loop may be modeled, as a practical matter, as a combination of transmission lines. Input and output transmission lines for carrying signals to and from the probe 100 are formed between a center conductor of a given loop (e.g., 102) and the inner surface of a conductive shield surrounding the center conductor. Another transmission line is formed between the two outer surfaces of the two halves of the loop 102, and is effectively terminated with a short circuit due to a ground plane 106 at the bottom of the probe 100. The outer surfaces of the conductive shields provide a path for the current on the inner surface of the conductive shields to flow around respective gaps 108 and 110 at the top of the loops 102 and 104, thereby forming a closed circuit.

The second transmission line is non-uniform, since the distance between the outer surfaces is not constant. However, it may be modeled accurately for purposes of computing input impedances by an equivalent 2-conductor, parallel-wire transmission line, with short-circuit termination. The thicknesses of the two equivalent conductors are the same as for the probe loops, and the length of the equivalent conductors is equal to the half-perimeter of the shielded loop, as measured on a centerline of the loop, including the ground plane "leg." The spacing between the two equivalent conductors is selected to make the area of the effective transmission line equal to the area of the actual shielded loop.

In accordance with an aspect of the present invention, the receive loop 104 can be rotated in small increments by a rotation element (not shown) to improve the orthogonality of the loops 102 and 104. For example, a high resolution micrometer can be used to incrementally rotate the coil along a plurality of positions within a limited arc. At each position, the coupling between the two loops 102 and 104 can be sampled to determine the degree of isolation between the loops. For example, the noise floor associated the frequency response of an associated in vivo sensor along a frequency range of interest can be determined at each position. Once the probe achieves a position of minimal coupling, more extensive measurements of the frequency response of the in vivo sensor can be taken.

Figure 4:
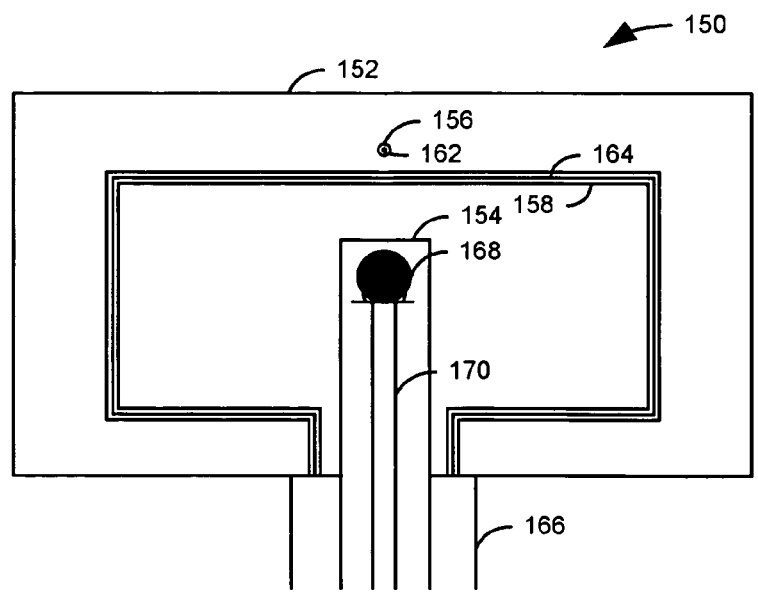
FIG. 4 illustrates a second exemplary implementation of a RF probe in accordance with an aspect of the present invention.

FIG. 4 illustrates a cross sectional view of a second exemplary implementation of a RF probe 150 in accordance with an aspect of the present invention. The probe 150 is implemented in a form 152 having a cavity 154 formed in or near its center. For example, the form 152 can be fashioned from polycarbonate or Teflon. A pair of orthogonal grooves 156 and 158 are provided within the form 152, and a conducting material, such as a coaxial cable or copper wire, can be placed within the grooves to form two orthogonal conducting loops 162 and 164. These loops can be connected to a control component (not shown) located, for example, within a base portion 166 supporting the form 152, opposite the first surface, or external to the form.

The system control can be used to direct one conducting loop (e.g., 162) to transmit a radio frequency (RF) signal at a desired frequency. The RF signal has an associated orientation, based on the orientation of the coil, such that the signal transmitted by the transmitting loop 162 is roughly orthogonal to an orientation associated with signals received at a receiving loop (e.g., 164). The transmitted signal is received at a sensor (not shown) which provides a response signal having in an orientation associated with the receiving loop 164. By analyzing the power of this response signal across a frequency range of interest, it is possible to determine both a resonant frequency associated with the sensor, and a noise floor for the frequency response, which indicates the amount of coupling between the transmitting loop 162 and the receiving loop 164.

It will be appreciated that the noise floor of the frequency response can be reduced by minimizing coupling between the transmitting loop 162 and the receiving loop 164. Coupling between the loops 162 and 164 will be minimized when the signal orientations associated with the loops are perfectly orthogonal. To this end, the cavity 154 in the form can include a ferrous bead 168 or magnet that influences the orientation associated with the RF signal provided by the transmitting loop 162. The ferrous bead or magnet 168 can be mechanically rotated via a rotation assembly 170 to shift the orientation of the RF signal transmitted by the transmitting loop 162. The rotation of the ferrous bead or magnet 168 can be controlled by the system control as to minimize the coupling detected between the transmitting loop 162 and the receiving loop 164.

Figure 5:
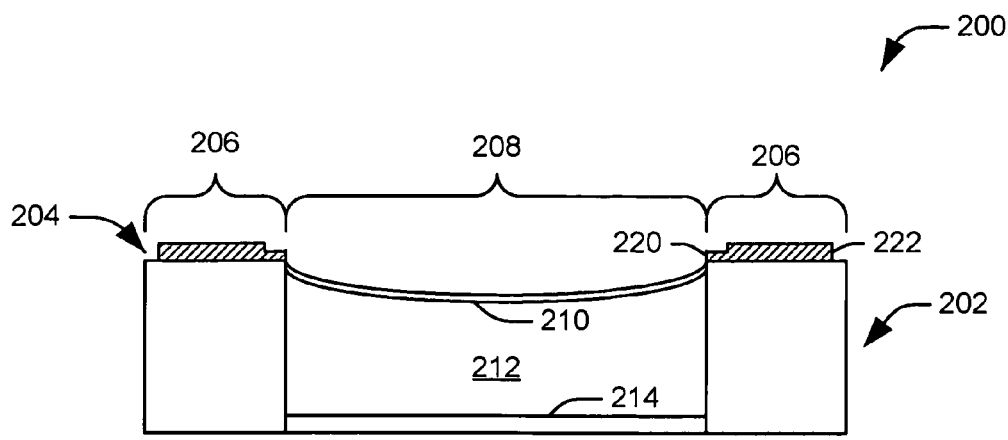
FIG. 5 illustrates an exemplary in vivo sensor in accordance with an aspect of the present invention.

FIG. 5 illustrates an exemplary in vivo sensor 200 in accordance with an aspect of the present invention. The illustrated sensor 200 is a pressure sensor, but the specific application and purpose of the sensor can vary in accordance with the present invention. The sensor includes a substrate 202 that can be comprised of a silicon material, but it will be appreciated that other materials may be used. The substrate 202 includes a contact surface 204 for making contact with a medium to be measured. For example, the contact surface 204 can be exposed to blood within an aneurysm sac or to aqueous humor within an eye. The surface 204 includes a non-compliant region 206 and a compliant region 208 that can be fabricated, for example, using MEMS techniques, as an impedance element, the impedance of which varies as the compliant region 208 changes shape. The compliant region 208 comprises a diaphragm 210 as one plate of a capacitive element that is separated by a dielectric 212 from another plate 214 of the capacitive element. As the pressure of the medium increases, the diaphragm plate 210 flexes closer to the other non-compliant plate 214 to change the capacitance of the capacitive element in proportion to the pressure exerted on the diaphragm plate 210. In the illustrated embodiment, the dielectric comprises air, but other suitably compliant dielectrics such as hydrogel, silicone, and various high dielectric oils, may also be used, without deviating from the principles of the present invention.

A region of conductive material 220 can be included as part of the substrate 202. The conductive material 220 is electrically coupled to the impedance element of the compliant region 208 (e.g., at the diaphragm 210) which is a capacitive element. The conductive material 220 is responsive to an external signal for energizing the impedance element so that the pressure may be determined. For example, the region of conductive material 220 can comprise an inductor coil 222 fabricated in the non-compliant region 206 of the contact surface 204 such that it is electrically coupled to the capacitive element to form a resonance or tank circuit In the present embodiment, the inductor coil 222 is formed by disposing conductive material in a predetermined pattern, like a concentric spiraled pattern, for example, in the non-compliant region 206. It should be understood that the inductor region need not be embodied solely at the non-compliant region 206 and may be embodied as part of the compliant region 208 as well without deviating from the principles of the present invention. In accordance with an aspect of the present invention, the resonant circuit comprising the inductor coil 222 and the capacitive element formed by the plates 210 and 214 may be excited into resonance by an external electromagnetic signal in the radio frequency (RF) range. Tank circuits of this type have a natural resonant frequency $f_o$ that, to the first order, depends of the values of the inductor and the capacitor as follows:

$$f_o = 1/2\pi(LC)^{1/2}$$

where L is the inductance and C is the capacitance.

Accordingly, as the capacitance of the sensor 200 changes, the resonant frequency $f_o$ of the tank circuit will change in proportion thereto.

Figure 6:
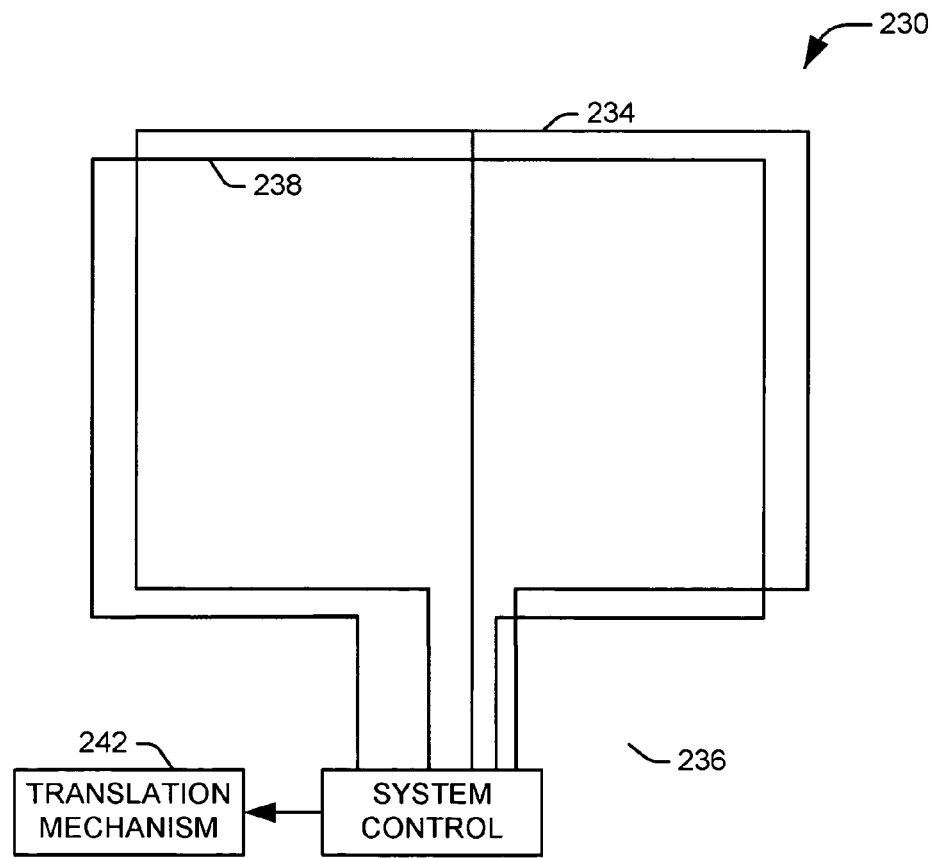
FIG. 6 illustrates a third exemplary implementation of an RF probe in accordance with an aspect of the present invention.

FIG. 6 illustrates a third exemplary implementation of an RF probe assembly 230 in accordance with an aspect of the present invention. In accordance with an aspect of the present invention, the probe assembly is implemented as a planar assembly, such that the coils are substantially parallel in orientation, but are configured as to minimize the mutual inductance between the coils. For example, the coils could be implemented as a printed circuit on one or more circuit boards. The probe includes a transmit coil 234, implemented on a first planar assembly (not shown), that receives a swept-frequency transmit signal from a system control 236. A response signal can be received at a receive loop 238, implemented on a second planar assembly (not shown), and provided back to the system control 236 for analysis or display to a human operator. In the absence of a nearby resonator, the response signal is a greatly reduced version of the transmit signal due to the inherent isolation resulting from the different current flow paths the orthogonal transmit and receive loops 234 and 238 which minimize the mutual inductance between the loops.

In accordance with an aspect of the present invention, respective first and second magnetic orientations (e.g., orientations of associated magnetic fields) of the transmit and receive coils 234 and 238 can be controlled by adjusting the relative position of the transmit and receive coils 234 and 238. To this end, a translation mechanism 242 is provided to mechanically adjust the relative position of the first and second planar assemblies. For example, the translation mechanism 242 can comprise a small motor that shifts a given planar assembly from side to side to change the relative position of the transmit and receive coils 234 and 238. The translation mechanism can be made responsive to the system control 236 to maintain the orthogonally of the magnetic orientations associated with the coils 234 and 238 by translating the position of at least one of the first and second planar assemblies as to minimize the detected coupling. Coupling between the loops can be minimized further by using a slotted ground plane between the loops. The loops may be spatially adjusted relative to each other to minimize coupling.

Figure 7:
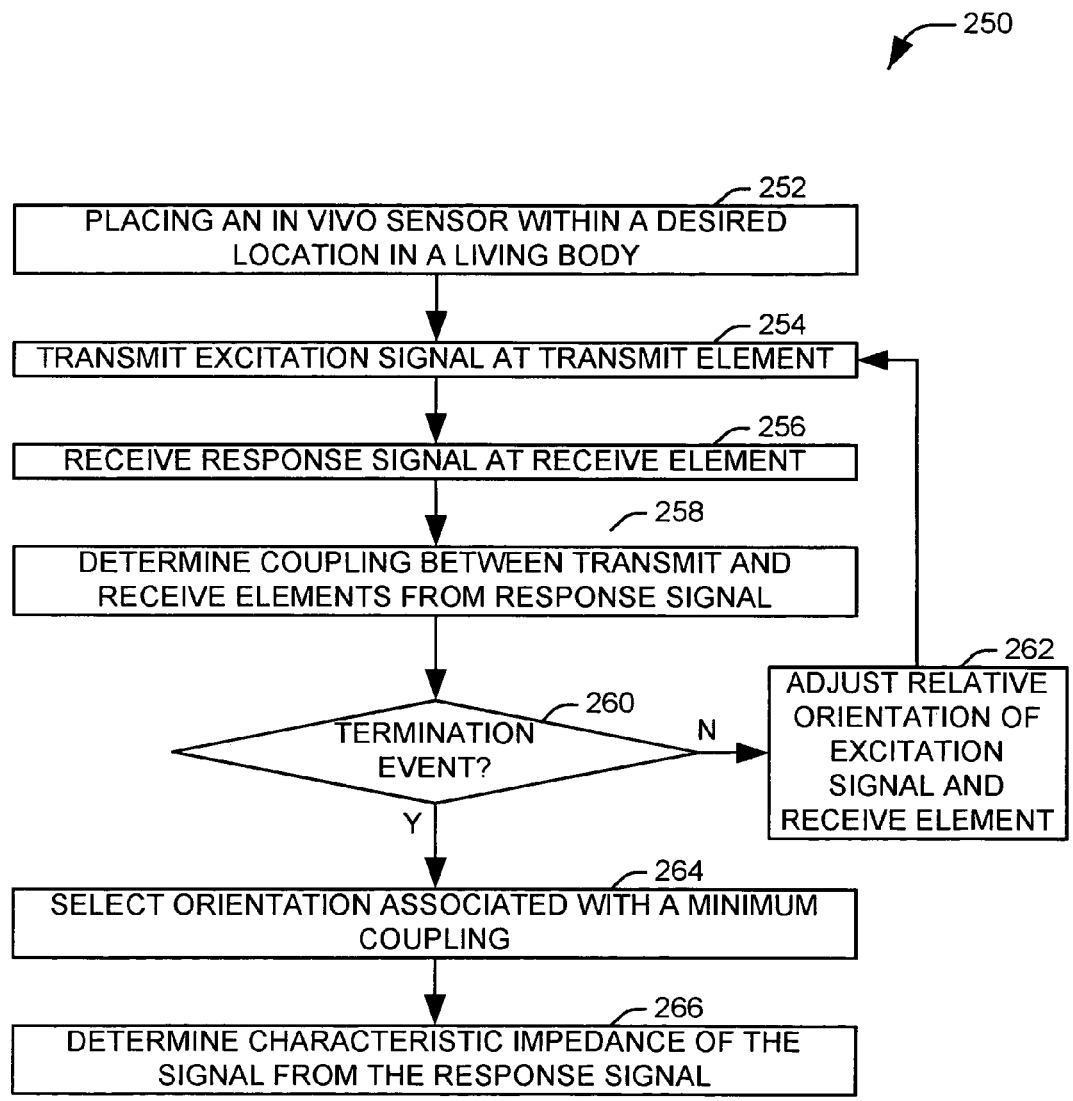
FIG. 7 illustrates an exemplary methodology for determining a characteristic of an in vivo sensor in accordance with an aspect of the present invention.

FIG. 7 illustrates an exemplary methodology 250 for determining a characteristic of an in vivo sensor in accordance with an aspect of the present invention. At step 252, the in vivo sensor is implanted at a desired location within a living body. For example, the sensor can be implanted within an aneurysm sac, in the aqueous humor of a human eye, inside of a hydrocephalic shunt, within an artificial joint, or along the surface of an orthopedic implant.

At step 254, a transmit signal, having a first orientation, is produced at a transmit element on a radio frequency (RF) probe. For example, the transmit element can provide an excitation signal that sweeps across a plurality of frequencies within a frequency range of interest. The excitation signal induces a response signal at the in vivo sensor. It will be appreciated that the magnitude of the response signal will approach a maximum value when the frequency of the excitation signal approaches a resonant frequency of the sensor. At other excitation frequencies, the response signal will remain at an associated noise floor. This noise floor is indicative of the degree of coupling between the transmit element and a receive element associated with the RF probe.

The response signal is received at the receive element at step 256. It will be appreciated that the receive element can have an associated second orientation that is substantially orthogonal to the first orientation, such that it is operative to receive signals having an orientation that is orthogonal or nearly orthogonal to the orientation of the excitation signal. The response signal can be analyzed at step 258 to determine an amount of coupling between the transmit element and the receive element. At 260, it is determined if a termination event has occurred. For example, the termination event can comprise the achievement of a coupling between the two coils that falls below a predetermined threshold or a predetermined number of measurements of the coupling (e.g., at a predetermined number of orientations of the transmit element and the receive element).

If the termination event has not occurred (N), the relative orientation of the excitation signal and the receive element is adjusted at step 262. For example, the transmit element or the receive element can be physically rotated to change the first orientation or the second orientation. Similarly, a magnetic element can be used to adjust the orientation of the excitation signal without changing the position of the transmit element. Once a new orientation has been selected, the methodology returns to step 254 to measure the coupling between the transmit and receive elements given the new orientation. If the termination event has occurred (Y), the methodology advances to step 264, where an orientation associated with a minimum coupling is selected. Once an orientation associated with minimum coupling is selected, a frequency response defined by the response signal can be analyzed to determine a resonant frequency or peak width associated with the frequency response. From this data, the characteristic impedance, quality factor, or other associated characteristic of the sensor can be determined from the response signal at step 266.

Figure 8:
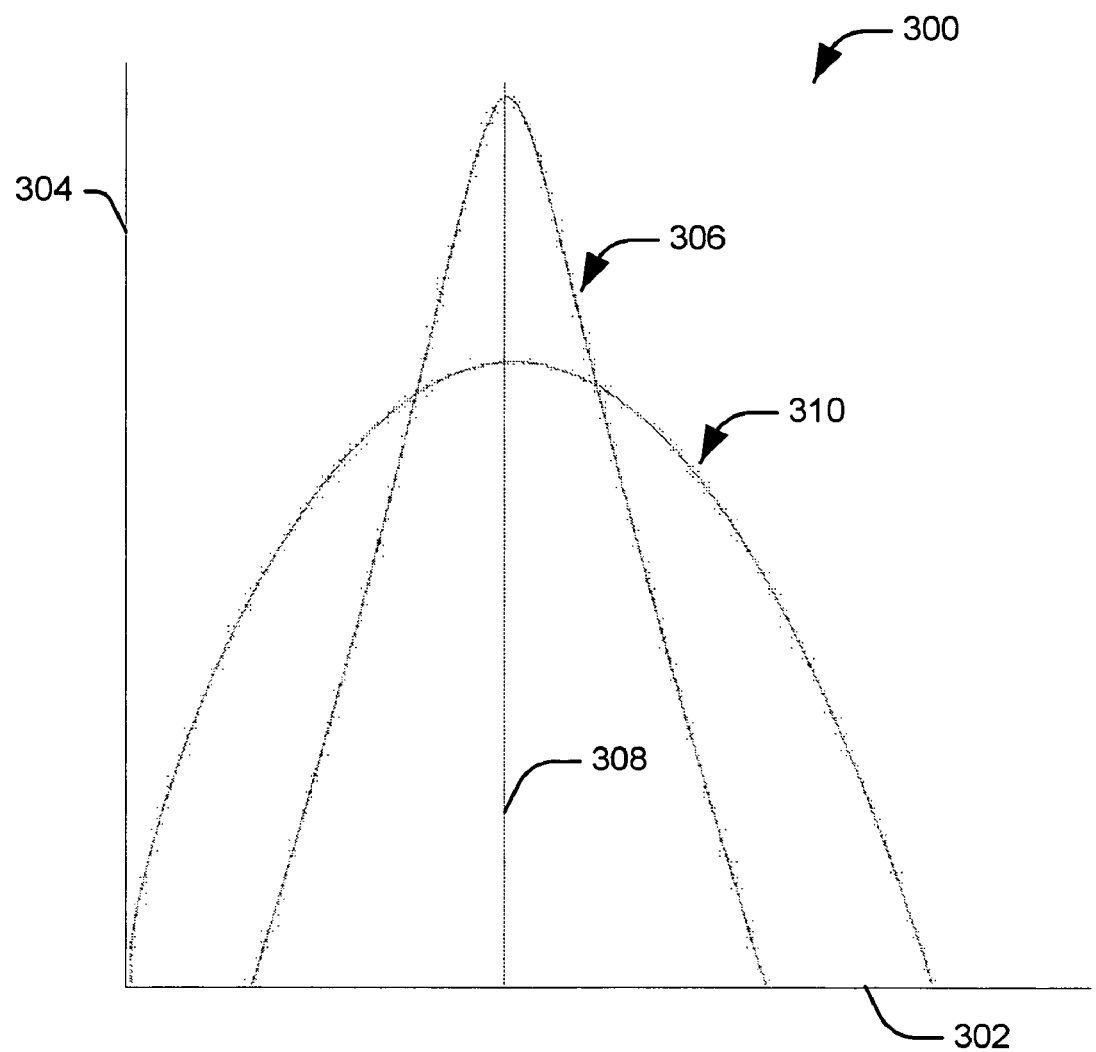
FIG. 8 illustrates a graph illustrating a frequency response of an in vivo sensor before and after a change in the quality factor of the sensor.

FIG. 8 illustrates a graph 300 illustrating a frequency response of an in vivo sensor under a first condition and a second condition, where the sensor has different quality factors in the first and second conditions. The graph 300 includes a horizontal axis 302 representing an interrogation frequency and a vertical axis 304 representing the amplitude of a response signal from the sensor. A first frequency response 306 represents the response of the sensor having a first quality factor. At a resonant frequency 308, the response 306 from the sensor reaches a peak amplitude. It will be appreciated that the peak is fairly narrow, reflecting a high quality factor associated with the first sensor.

A second frequency response 310 represents the response of the sensor, with a second quality factor. It will be appreciated that the sensor can be designed such that a characteristic of the sensor influencing the quality factor, such as a resistor, inductor or capacitor of the sensor, changes with a physical quality inside the body (e.g., pressure, temperature, etc.). The peak frequency response of the sensor in the second condition is significantly blunted relative to the response of the sensor in the first condition. The greater peak width of the frequency response indicates a decrease in the quality factor associated with the sensor.

From the above description of the invention, those skilled in the art will perceive improvements, changes, and modifications. For example, it is contemplated that the present invention could be adapted to diagnose a number of degenerative eye disorders by measuring other characteristics of various structures of the eye, both within and external to the retina. Such improvements, changes, and modifications within the skill of the art are intended to be covered by the appended claims.

Having described the invention, we claim:

1. A method for determining a characteristic of an in vivo sensor, comprising:

generating a transmit field, operative to induce a response signal in an associated in vivo sensor, at a transmitting component having an associated orientation;

receiving the response signal at a receiving component, having an associated orientation;

measuring the coupling between the transmitting component and the receiving component from the received response signal, wherein measuring the coupling comprises determining a noise floor of the received response signal; and rotating the associated orientation of at least one of the transmitting component and the receiving component as to reduce the measured coupling.

2. The method of claim 1, further comprising sweeping an associated frequency of the transmit field across a desired frequency range, and measuring the response signal at the receiving component at each of a plurality of frequencies.

3. The method of claim 2, further comprising determining a characteristic impedance of the associated in vivo sensor from the measured response signal at each of the plurality of frequencies.

4. The method of claim 2, further comprising determining a quality factor associated with the in vivo sensor from the measured response signal at each of the plurality of frequencies.

5. The method of claim 1, wherein rotating the associated orientation of at least one of the transmitting component and the receiving component includes physically rotating at least one of the transmitting component and the receiving component.

6. The method of claim 1, wherein rotating the associated orientation of at least one of the transmitting component and the receiving component includes rotating an associated magnetic element to shift the associated orientation of the transmitting component.

7. The method of claim 1, the in vivo sensor comprising a pressure sensor.

8. The method of claim 1, wherein the associated orientation of the transmitting component is substantially orthogonal to the associated orientation of the receiving component.

9. A method for determining a characteristic of an in vivo sensor, comprising:

generating a transmit field, operative to induce a response signal in an associated in vivo sensor, at a transmit coil oriented in a first plane;

receiving the response signal at a receive coil, oriented in a second plane that is substantially orthogonal to the first plane;

measuring the coupling between the transmit coil and the receive coil from the received response signal, wherein measuring the coupling comprises determining a noise floor of the received response signal; and rotating at least one of the transmit coil and the receive coil as to reduce the measured coupling.

\* \* \* \* \*